(12) United States Patent
Wong

(10) Patent No.: US 7,264,005 B2
(45) Date of Patent: Sep. 4, 2007

(54) TOOTHPICK DEVICE

(76) Inventor: Thomas K. Wong, 795 Panorama Dr., San Francisco, CA (US) 94131

( * ) Notice: Subject to any disclaimer, the term of this patent is extended or adjusted under 35 U.S.C. 154(b) by 0 days.

(21) Appl. No.: 11/234,780

(22) Filed: Sep. 23, 2005

(65) Prior Publication Data

US 2007/0068549 A1    Mar. 29, 2007

(51) Int. Cl.
A61C 15/00 (2006.01)
(52) U.S. Cl. .................................................. 132/321
(58) Field of Classification Search ............... 132/321, 132/329; D28/65
See application file for complete search history.

(56) References Cited

U.S. PATENT DOCUMENTS

| | | | | |
|---|---|---|---|---|
| 24,691 | A | * | 7/1859 | McChesney ................ 139/421 |
| 195,664 | A | * | 9/1877 | Smith ......................... 132/328 |
| 361,775 | A | | 4/1887 | Nellis |
| 407,362 | A | * | 7/1889 | Mason ........................ 132/321 |
| 469,064 | A | | 2/1892 | McKay |
| D24,691 | S | | 9/1895 | McChesney |
| 656,479 | A | * | 8/1900 | Schellenbach .............. 132/321 |
| 710,498 | A | | 10/1902 | McClain |
| 774,253 | A | * | 11/1904 | Keefe ......................... 132/329 |
| 1,746,591 | A | * | 2/1930 | Heymann et al. ........... 132/329 |
| 1,927,455 | A | * | 9/1933 | John .......................... 132/329 |
| 1,997,877 | A | * | 4/1935 | Spanel ........................ 132/321 |
| 3,978,872 | A | | 9/1976 | Bond |
| 4,304,245 | A | * | 12/1981 | Lichfield .................... 132/321 |
| D270,100 | S | | 8/1983 | Hjalmarsson |
| 4,570,653 | A | | 2/1986 | Wolf |
| 4,577,649 | A | | 3/1986 | Shimenkov |
| 4,651,760 | A | | 3/1987 | Reipur |
| 4,800,905 | A | | 1/1989 | Stuart |
| 4,805,646 | A | | 2/1989 | Shimenkov |
| 4,922,936 | A | | 5/1990 | Buzzi et al. |
| D309,042 | S | | 7/1990 | Renno |
| 5,609,170 | A | * | 3/1997 | Roth .......................... 132/329 |
| 5,704,388 | A | | 1/1998 | Freeman |
| 5,823,208 | A | | 10/1998 | Lin |
| D437,459 | S | | 2/2001 | Inaba |
| 2005/0098193 | A1 | | 5/2005 | Tsaur |
| 2006/0065283 | A1 | * | 3/2006 | Shaygan ..................... 132/329 |

FOREIGN PATENT DOCUMENTS

DE      3130971 A1 *  2/1983

* cited by examiner

*Primary Examiner*—Robyn Doan
(74) *Attorney, Agent, or Firm*—Thomas R. Lampe

(57) ABSTRACT

A toothpick device in the form of an elongated, hollow member having a readily deformable central portion and readily deformable spaced end portions formed by two attached, convexly curved, flexible walls having an elastic memory.

16 Claims, 3 Drawing Sheets

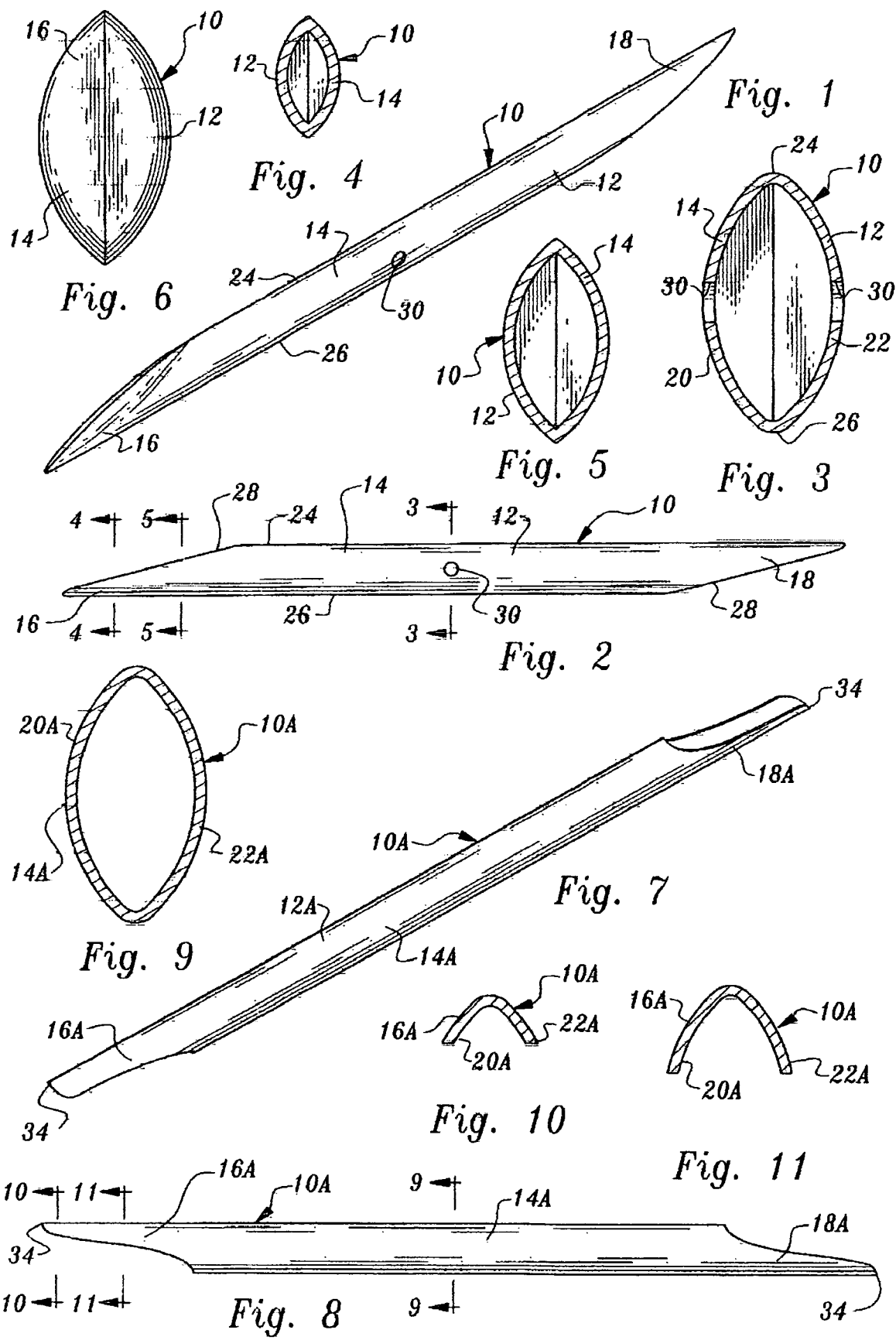

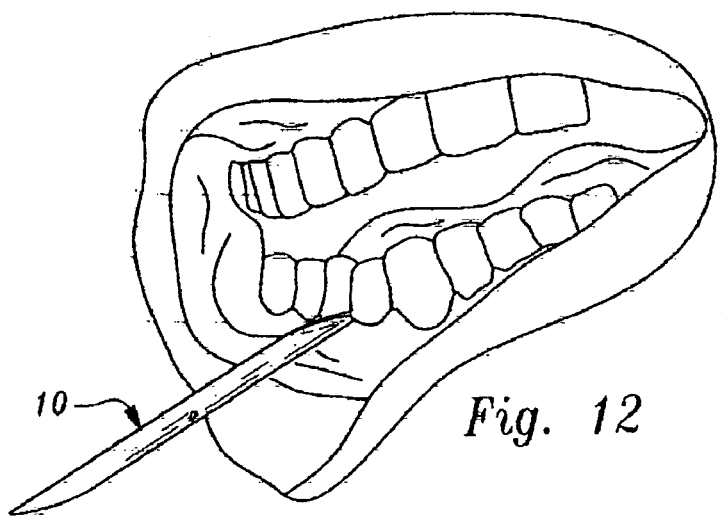
Fig. 12
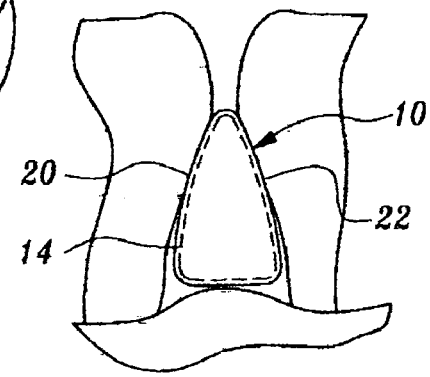
Fig. 13
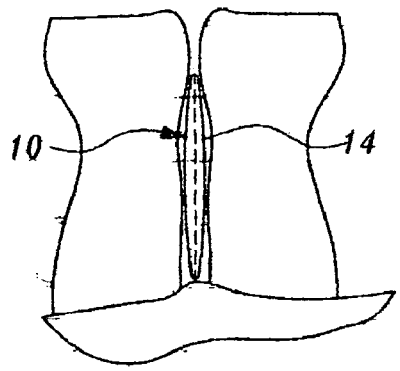
Fig. 14
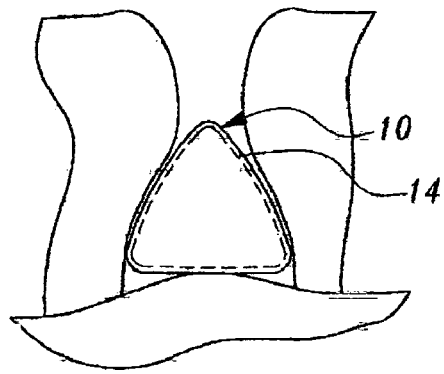
Fig. 15
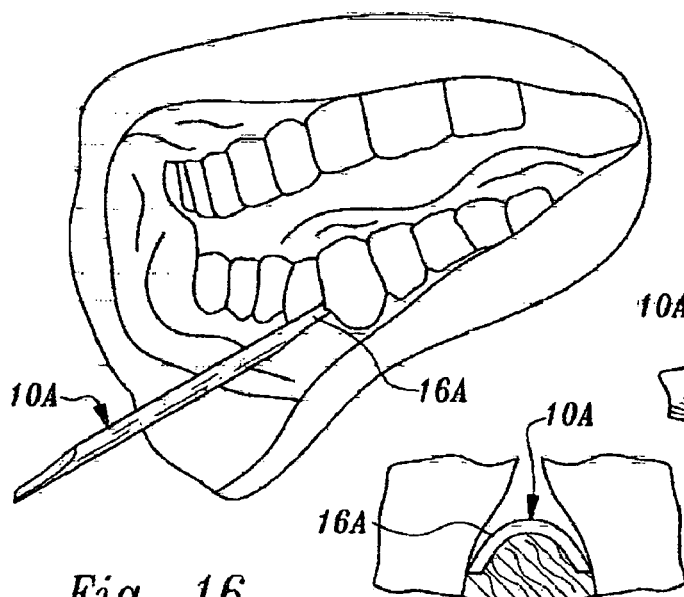
Fig. 16
Fig. 18
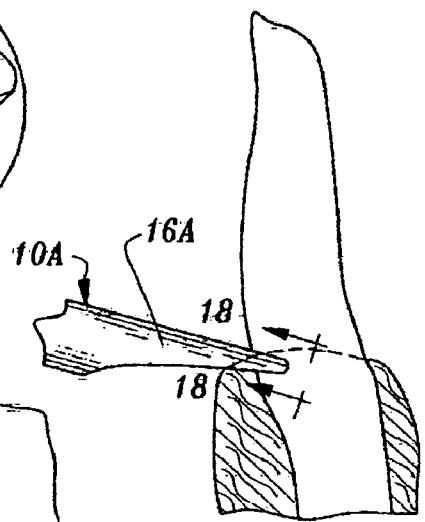
Fig. 17

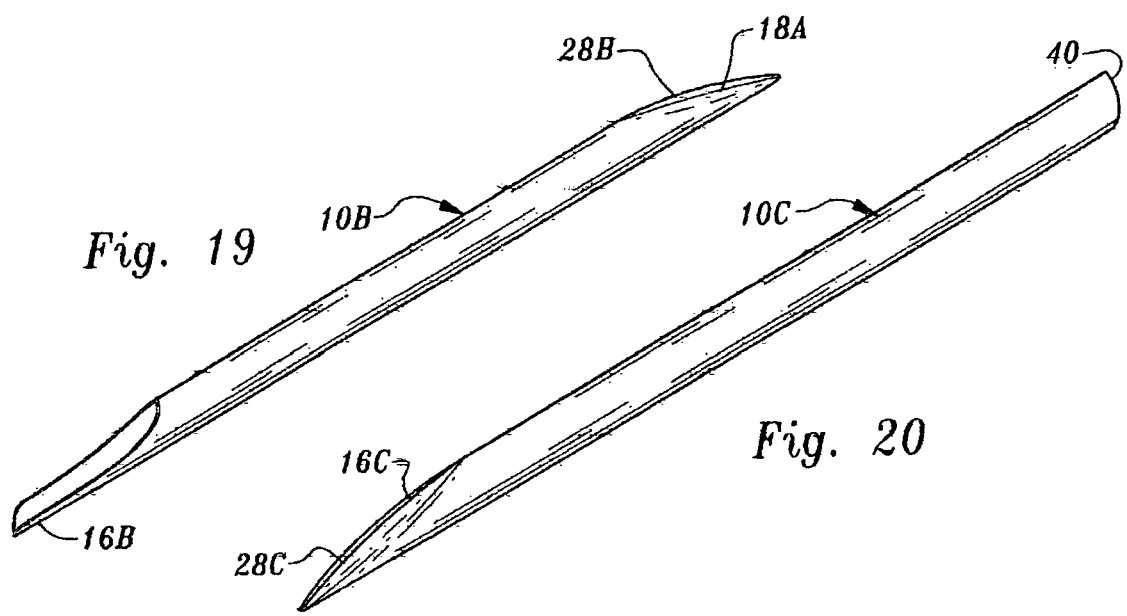
Fig. 19
Fig. 20
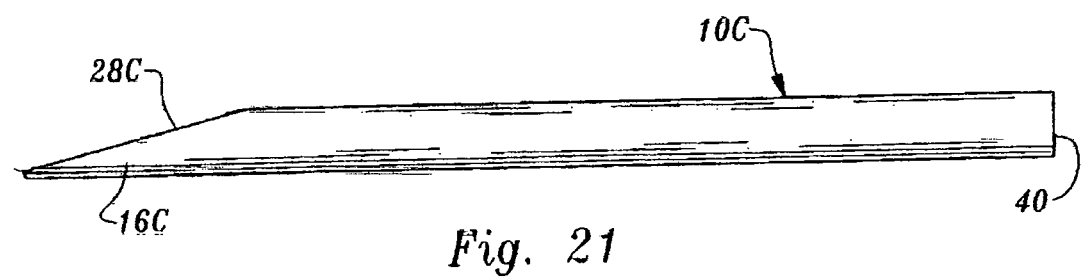
Fig. 21
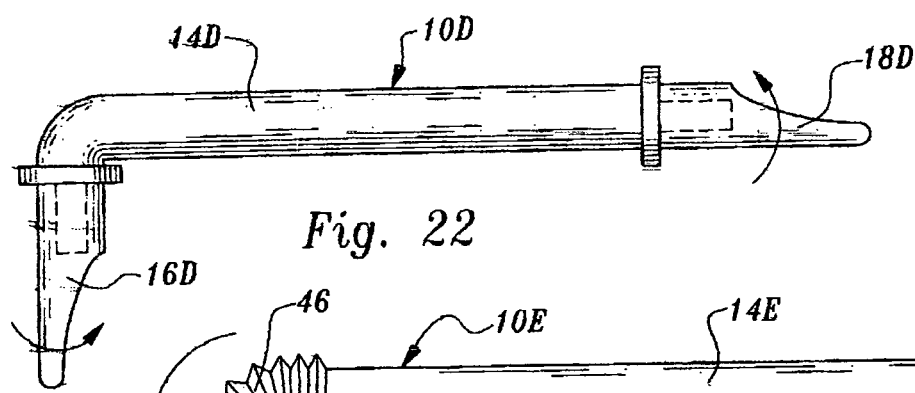
Fig. 22
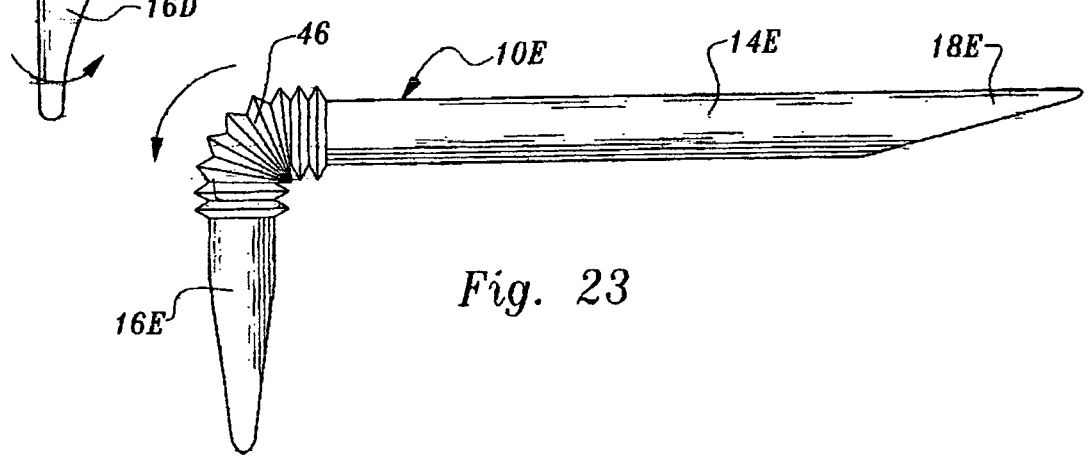
Fig. 23 ically limited, making it difficult for them to be utilized in tooth gaps narrower than the width of the toothpick. If a user is not careful, the solid toothpick may loosen the teeth.
TOOTHPICK DEVICE

TECHNICAL FIELD

This invention relates to a toothpick device for cleaning teeth, removing plaque therefrom and stimulating gums.

BACKGROUND OF THE INVENTION

Toothpicks per se are well known devices for cleaning teeth and removing plaque and debris therefrom. Conventionally, toothpicks are of solid construction, being made of solid materials such as wood or plastic. The compressibility of these solid materials is extremely limited, making it difficult for them to be utilized in tooth gaps narrower than the width of the toothpick. If a user is not careful, the solid toothpick may loosen the teeth.

Hard solid materials also create uncomfortable sensations after use and have limited ability to bend and tend to break easily. Solid toothpicks cannot change their shape to conform to the various shapes and sizes of tooth gaps, thus reducing their effectiveness with regard to plaque removal.

It is known to incorporate bristles on toothpicks. While these can be significantly better than solid toothpicks in terms of fitting into gaps between the teeth and provide better cleaning, fabrication cost is significantly higher. Further, the size of the core holding the bristles and the bristles themselves make the toothpicks difficult to position into narrow gaps. Like the solid toothpicks, bristle toothpicks do not lend themselves to effectively cleaning below the gum line.

Toothpick structures exist which have rather specific shapes aimed at improving the performance of solid material constructions. U.S. Pat. No. 3,978,872 discloses a toothpick that is provided with a pair of hollow-ground surfaces terminating in a thin bladed end. U.S. Pat. No. 5,823,208 discloses a flexible integral toothpick structure for gum massaging and teeth cleaning purposes having one end provided with a fixed reverse U-shaped end and a second end provided with a flat extension on which are disposed a number of V-shaped marks for massaging the gum. A slant pointed projection is employed in connection with the flat extension to pick out food residues left between molar teeth. U.S. Pat. No. 4,651,760 discloses a toothpick made from solid plastic material having a variety of features aimed at improving the effectiveness of the solid construction.

U.S. Pat. No. 4,577,649 discloses a toothpick which may be elastic in transverse direction and may be solid, hollow or composed of two connected strips. The toothpick has two faces which are inclined relative to one another so as to form an acute angle therebetween and a sharp upper edge. A third face connects the side faces with one another providing a generally triangular configuration and forms two sharp lower edges.

The device of U.S. Pat. No. 4,577,649 has drawbacks. The triangular shaped cross-section and the two lower edges limit the compressibility of the toothpick making it difficult to position into narrow gaps. The triangular shape also limits the toothpick's ability to expand to clean larger gaps. The triangular shape makes the structure difficult to bend to allow the toothpick to reach back teeth. A user has very limited ability to adjust the cross-section size of the toothpick to make it better conform to the various types of tooth gaps. Due to the great variations in shapes and sizes of tooth gaps, even for one user, a single cross-section is not adequate or very effective to clean above and below the gum line at the same time. Finally, the toothpick disclosed in U.S. Pat. No. 4,577,649 would be very costly to produce, resulting in a poor benefit/cost ratio and questionable commercial viability.

DISCLOSURE OF INVENTION

The present invention relates to a toothpick device for cleaning teeth, removing plaque therefrom and stimulating gums.

The toothpick device is of unitary construction and comprises an elongated, hollow member having a central portion and spaced end portions formed by two attached, convexly curved, flexible walls having an elastic memory.

The central portion has a generally ovoid cross-sectional configuration wherein the walls converge to form two, spaced, opposed, elongated lines of intersection.

The walls taper at least one of the end portions to facilitate entry of the toothpick device between adjacent teeth, the walls adapted to compress inwardly toward one another upon such entry to generally conform to the shape of a gap between adjacent teeth receiving the toothpick device.

Other features, advantages and objects of the present invention will become apparent with reference to the following description and accompanying drawings.

BRIEF DESCRIPTION OF DRAWINGS

FIG. 1 is a perspective view of a first embodiment of the toothpick device of the present invention;

FIG. 2 is a side, elevational view of the toothpick device of FIG. 1;

FIG. 3 is a greatly enlarged, cross-sectional view taken along the line 3-3 of FIG. 2;

FIGS. 4 and 5 are respectively, greatly enlarged, cross-sectional views taken along lines 4-4 and 5-5 of FIG. 2;

FIG. 6 is an end elevational view of the toothpick device of FIG. 1;

FIG. 7 is a view similar to FIG. 1, but illustrating an alternative embodiment of the invention;

FIG. 8 is a view similar to FIG. 2, but illustrating the embodiment of FIG. 7;

FIG. 9 is a greatly enlarged, cross-sectional view taken along the line 9-9 of FIG. 8;

FIGS. 10 and 11 are, respectively, greatly enlarged, cross-sectional views taken along lines 10-10 and 11-11 of FIG. 8;

FIG. 12 is a perspective view illustrating the toothpick device embodiment of FIG. 1 applied to teeth and gum of an individual;

FIG. 13 is a diagrammatic view of the first embodiment positioned in a medium sized gap formed by two teeth and gum;

FIG. 14 illustrates the toothpick device embodiment of FIG. 1 located in a narrow gap;

FIG. 15 shows the toothpick device embodiment of FIG. 1 positioned in a wide gap;

FIG. 16 is a view similar to FIG. 12, but illustrating the second embodiment of the toothpick device applied to the user's teeth and gum;

FIG. 17 is a somewhat diagrammatic view showing a cross-section of the user's gum, a tooth projecting therefrom and the tapered end portion of the toothpick device embodiment of FIG. 7 being utilized to clean the teeth walls below the gum line and to massage the gum;

FIG. 18 is an enlarged cross-sectional view taken along the line 18-18 of FIG. 7;

FIG. 19 is a perspective view of a third embodiment of the toothpick device;

FIG. 20 is a perspective view of a fourth embodiment of the toothpick device;

FIG. 21 is a side, elevational view of the embodiment of FIG. 20;

FIG. 22 is a side, elevational view of a fifth embodiment of the toothpick device; and FIG. 23 is a side, elevational view of a sixth embodiment of the toothpick device.

MODES FOR CARRYING OUT THE INVENTION

Referring now to FIGS. 1-6 and 12-15, a toothpick device 10 constructed in accordance with the teachings of the present invention is illustrated. The toothpick device is utilized for cleaning teeth, removing plaque therefrom and stimulating gums. Toothpick device 10 is of unitary construction and comprises an elongated, hollow member 12 of generally tubular construction having a central portion 14 and spaced end portions 16, 18.

The central portion and spaced end portions are formed by two attached, convexly curved, thin, flexible walls 20, 22 having an elastic memory.

The central portion 14 has a generally ovoid cross-sectional configuration wherein the walls 20, 22 converge to form two, spaced, opposed, elongated lines of intersection 24, 26, and rounded corners extending along said lines of intersection.

Walls 20, 22 taper at the end portions to form generally ovoid cross-sectional configurations smaller than the generally ovoid cross-sectional configuration of the central portion to facilitate entry of the toothpick device between adjacent teeth and engage the gum. In this embodiment of the application, in both of the end portions interconnecting opposed edges of the tapering walls meet at a joint 28.

The end portions 16, 18 are used to engage and stimulate the gum and to effect cleaning of the plaque on the teeth at and above the gum line, as illustrated in FIG. 12. Either of the end portions may be utilized for such purpose. The tapered walls of end portions 16, 18 in this embodiment form blunt points disposed on opposed sides of the central portion primary axis.

Cleaning between the teeth is accomplished by further inserting the toothpick device within a tooth gap so that one of the end portions 16, 18 or the central portion 14 is disposed therein.

FIGS. 13-15 show the toothpick device in three gaps of different sizes. An important aspect of the present invention resides in the ability of the central portion and the end portions to deform to conform to the shape of the gap as defined by adjoining teeth and the gum. FIG. 13 shows a representative shape of the central portion in a medium sized gap, while FIGS. 14 and 15 show the representative shapes assumed by the central portion respectively in narrow and wide gaps. Similar deformation will occur at the end portions when they engage the teeth and compressive forces are exerted thereon. In all cases, direct contact is made with the inner surfaces of the adjoining teeth as well as the gum at the gap location. Moving of the toothpick device with the central portion or end portions so disposed in a gentle in-in-out motion cleans between the teeth and movement side-to-side can be accomplished to expand the tooth contact areas for even more plaque removal.

By separating the above and below gum line cleaning into two distinct processes, the toothpick device achieves excellent results and highly satisfying cleaning. If desired, the outer surfaces of walls 20 and 22 can be micro-textured or coated with other surfaces such as rubber to enhance removal of the plaque. Flavors such as fresh mint can be added to provide an improved experience for the user.

Toothpick device 10 has two openings 30 formed in the central portion 14 to allow for the passage of air into and out of the otherwise completely enclosed elongated, hollow member so that deformation of the walls can readily occur.

Referring now to FIGS. 7-11 and 16-18, a second toothpick device embodiment 10A is illustrated. In this embodiment of the invention both of the end portions 16A and 18A are open so that the interior of the hollow member 12A communicates with the ambient atmosphere at the ends thereof. Thus, there is no need for an air passage opening such as opening 30 in the first embodiment described above.

The walls 20A, 22A of this second embodiment taper at the end portions as shown, the walls tapering both in the direction of the primary axis of the central portion and in a direction generally orthogonal thereto. That is, the tapered walls form end portions which become smaller in both the vertical and horizontal direction in the direction of the distal ends thereof where they converge at a blunt point 34. This is shown in the cross-sectional representations of FIGS. 10 and 11 with respect to end portion 16A. FIGS. 16-18 provide a good illustration as to how the edges of the open end portion 16A effectively engage the gum and go below the gum line adjacent to the teeth to provide more effective plaque cleaning.

If desired, one of the end portions can be closed and the other open, rather than both being open or both being closed. FIG. 19 shows a third embodiment of the toothpick device 10B wherein an end portion 16B is open and end portion 18B is closed by a joint 28B.

A fourth embodiment illustrated in FIGS. 20 and 21 is designated by reference numeral 10C and includes an open, non-tapered end 40, end portion 16C being closed by a joint 28C. Open end 40 allows venting during distortion of the toothpick device 10C during use.

FIG. 22 illustrates yet another embodiment of the toothpick device, this alternative embodiment being designated by reference numeral 10D. In this embodiment of the invention, end portions 16D and 18D are not integral with the central portion 14D. Instead, the end portions 16D, 18D are rotatably mounted in any desirable manner at the ends of central portion 14D. In addition, the end portion primary axis of end portion 18D is substantially co-axial with the central portion primary axis while the end portion primary axis of end portion 16D forms an angle with the primary end portion axis of end portion 18D and the central portion primary axis.

FIG. 23 illustrates yet another embodiment of the toothpick device 10E wherein a flexible pleated-type connector 46 connects end portion 16E to the central portion 14E so that the angle between the end portion primary axis of end portion 16E relative to the central portion primary axis can be varied.

The invention claimed is:

1. A toothpick device for cleaning teeth, removing plaque therefrom and stimulating gums, said toothpick device being of unitary construction and comprising a double-ended, elongated, hollow member having a central portion and spaced end portions formed by two attached, convexly curved, flexible walls of predetermined shape having an elastic memory, said central portion having a central portion primary axis and a generally ovoid cross-sectional configuration formed by said walls converging to form two, spaced, opposed, elongated lines of intersection extending substantially the full length of said elongated hollow member and extending parallel to one another along said central portion, said walls both tapering at at least one of said end portions in a direction extending away from said central portion to form a tapered end portion facilitating entry of the toothpick device between adjacent teeth, one of said elongated lines of intersection at said tapered end portion converging toward the other elongated line of intersection at said tapered end portion, said walls adapted to compress inwardly toward one another and to bend about and along both of said elongated lines of intersection upon such entry and while positioned between said adjacent teeth to generally conform to the shape of a gap between said adjacent teeth receiving the toothpick device, and the elastic memory of said walls causing said walls to be maintained in frictional engagement with said adiacent teeth and gum adjoining said adjacent teeth during movement of the toothpick device between said adjacent teeth, the elastic memory of said walls further causing the walls to return to their predetermined shape after the toothpick device is removed from said gap, said tapered end portion being closed and having a generally ovoid cross-sectional configuration smaller than the generally ovoid cross-sectional configuration of said central portion.

2. The toothpick device according to claim 1 wherein at least one of said end portions is open and has a generally U-shaped configuration.

3. The toothpick device according to claim 1 wherein both of said end portions are closed and wherein at least one opening is formed in said elongated hollow member to allow for the passage of air into and out of said hollow member.

4. The toothpick device according to claim 1 wherein said walls form rounded corners extending along said lines of intersection.

5. The toothpick device according to claim 1 wherein interconnecting opposed edges of the walls at said tapered end portion meet at a joint defined by said elongated line of intersection converging toward the other elongated line of intersection.

6. The toothpick device according to claim 1 wherein said walls at said tapered end portion taper both in the direction of said central portion primary axis and in a direction generally orthogonal thereto.

7. The toothpick device according to claim 6 wherein said walls at said tapered end portion converge to form a blunt point.

8. The toothpick device according to claim 1 wherein both of said end portions are tapered end portions, with each of said tapered end portions having an end portion primary axis, the primary end portion axes of said tapered end portions being substantially coaxial with one another and with said central portion primary axis.

9. The toothpick device according to claim 8 wherein said walls at both of said tapered end portions converge to form blunt point, said blunt points disposed on opposed sides of said central portion primary axis.

10. The toothpick device according to claim 1 wherein said walls taper at both of said end portions are tapered end portions, with each of said tapered end portions having an end portion primary axis, the primary end portion axes of said tapered end portions being angularly disposed relative to one another.

11. The toothpick device according to claim 10 wherein the end portion primary axis of one of said tapered end portions is substantially coaxial with said central portion primary axis.

12. The toothpick device according to claim 1 wherein at least one of said end portions is movably mounted relative to said central portion.

13. The toothpick device according to claim 1 wherein at least one of said end portions is rotatably mounted relative to said central portion.

14. The toothpick device according to claim 1 additionally comprising a flexible connector connecting at least one of said end portions to said central portion to allow relative movement therebetween.

15. The toothpick device according to claim 1 wherein the walls are thin plastic walls.

16. The toothpick device according to claim 1 wherein said double-ended, elongated hollow member defines an interior and has at least one opening allowing for passage of air into and out of said interior when said walls change shape.

* * * * *